United States Patent
Perkins et al.

(10) Patent No.: US 6,224,583 B1
(45) Date of Patent: May 1, 2001

(54) AIR VENTING IN OPHTHALMIC IRRIGATION/ASPIRATION SYSTEM VIA CLOSED BAG SYSTEM

(75) Inventors: James T. Perkins, County of St. Charles; Jeffery A. Knight; William J. Neubert, both of County of St. Louis, all of MO (US)

(73) Assignee: Bausch & Lomb Surgical, Inc., Claremont, CA (US)

( * ) Notice: Subject to any disclaimer, the term of this patent is extended or adjusted under 35 U.S.C. 154(b) by 0 days.

(21) Appl. No.: 09/173,453

(22) Filed: Oct. 15, 1998

(51) Int. Cl.[7] ................................................. A61B 19/00
(52) U.S. Cl. ............................................. 604/408; 604/35
(58) Field of Search ..................................... 604/405, 408, 604/27, 35, 45; 383/41; 206/205, 438; 55/261, 286, 287, 361, 365, 368, 381, 379, DIG. 1

(56) References Cited

U.S. PATENT DOCUMENTS

| | | |
|---|---|---|
| 4,117,843 | 10/1978 | Banko . |
| 4,773,897 | 9/1988 | Scheller et al. . |
| 4,813,428 * | 3/1989 | Muraki et al. ................... 128/721 |
| 4,935,005 * | 6/1990 | Haines ............................ 604/30 |
| 5,035,516 * | 7/1991 | Pacheco .......................... 383/41 |
| 5,267,956 | 12/1993 | Beuchat . |
| 5,380,314 | 1/1995 | Herweck et al. ................. 604/403 |
| 5,505,306 * | 4/1996 | Akemi et al. ................... 206/438 |
| 5,685,840 * | 11/1997 | Schechter et al. ............... 604/22 |
| 5,746,719 * | 5/1998 | Farra et al. ..................... 604/151 |
| 5,810,765 | 9/1998 | Oda .............................. 604/31 |
| 5,853,247 * | 12/1998 | Shroyer .......................... 383/95 |
| 5,964,404 * | 10/1999 | Randolph ........................ 239/56 |
| 6,119,855 * | 12/1998 | Yeager et al. ................... 206/213.1 |

FOREIGN PATENT DOCUMENTS

| | | |
|---|---|---|
| 1 263 111 | 2/1972 | (GB) . |
| WO 89/03230 | 10/1988 | (WO) . |
| WO 90/00908 | 4/1989 | (WO) . |
| WO 98/18507 | 10/1997 | (WO) . |

* cited by examiner

Primary Examiner—Richard K. Seidel
Assistant Examiner—Cris Rodriquez
(74) Attorney, Agent, or Firm—Grant Kang

(57) ABSTRACT

An ophthalmic irrigation/aspiration venting system that vents a portion of an aspiration circuit by drawing sterile air from a bag. The bag is provided with an air reservoir member to ensure that an adequate air volume is available.

5 Claims, 2 Drawing Sheets

AIR VENTING IN OPHTHALMIC IRRIGATION/ASPIRATION SYSTEM VIA CLOSED BAG SYSTEM

BACKGROUND OF THE INVENTION

1. Field of the Invention

This invention relates to air venting in an ophthalmic irrigation/aspiration system via a closed bag system and to a structure for a closed bag used in an ophthalmic irrigation/aspiration system.

2. Related Art

The Storz Millennium Microsurgical System uses a venturi pump for irrigation and aspiration. When venting is in progress for the irrigation/aspiration aspects of the microsurgical system, air is drawn through the pump, through the bag and into the aspiration circuit. The air that is drawn is ambient air.

The Phacotron Gold microsurgical system also employs air venting. In this system, a T is provided into an aspiration circuit. The T provides direct access to the ambient air and is controlled by a pinch valve. During venting, the controlling pinch valve is opened which permits ambient air to flow directly into the aspiration circuit and relieve residual pressure.

There is no known venting system which provides a sterile volume of venting air. In addition, there is no known system which divides an aspiration circuit and air vents one of these divided sections.

There is a need in the art to provide a system that draws sterile air from, not through, the bag to accomplish venting.

There is a further need in the art to provide a bag with an air reservoir member for guaranteeing a supply volume of sterile air.

SUMMARY OF THE INVENTION

It is in view of the above problems that the present invention was developed. The invention is a venting system that vents a portion of an aspiration circuit by drawing sterile air from a bag. The bag is provided with an air reservoir member to ensure that an adequate air volume is available.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE PREFERRED EMBODIMENTS

Figure 1:
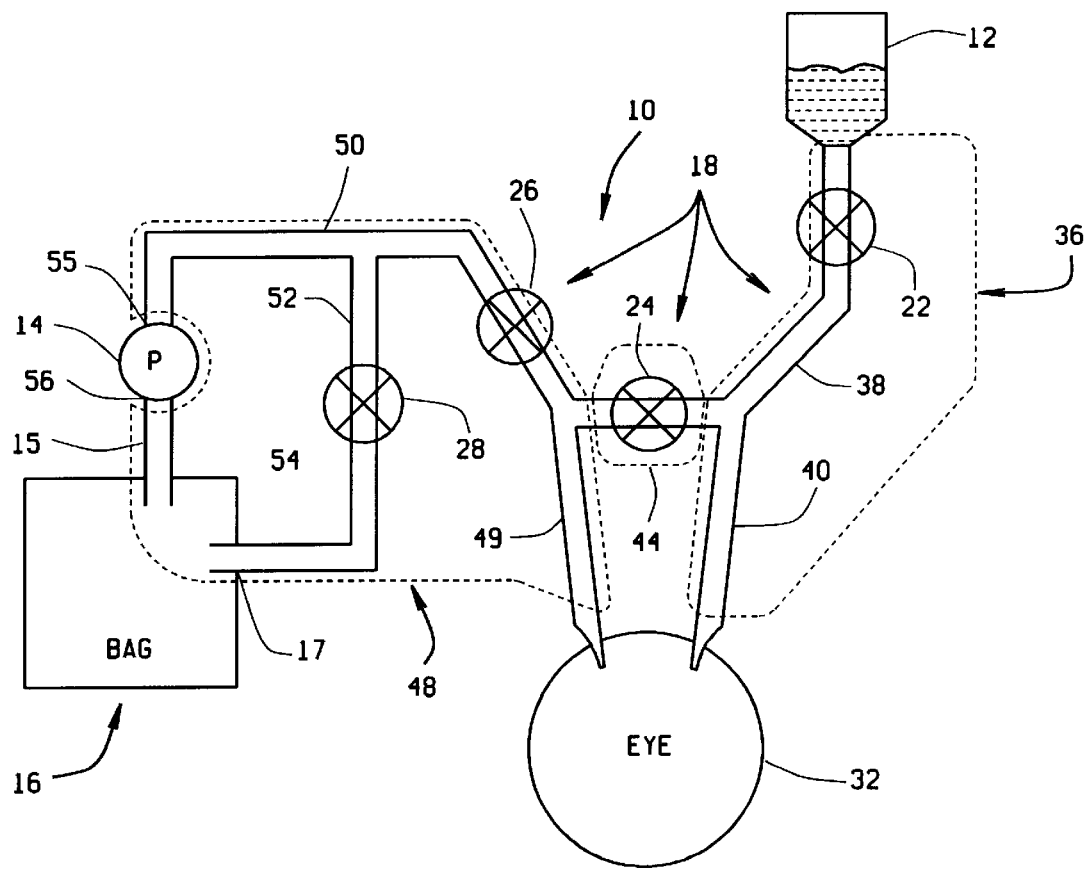
FIG. 1 illustrates an ophthalmic irrigation/aspiration system in accordance with the present invention.

Referring to the accompanying drawings in which like reference numbers indicate like elements, FIG. 1 illustrates an ophthalmic irrigation/aspiration system shown generally at 10. Ophthalmic irrigation/aspiration system 10 includes bottle 12, pump 14, bag 16, and irrigation/aspiration circuit 18.

Located variously throughout irrigation/aspiration circuit 18 for controlling fluid communication are irrigation pinch valve 22, bridge pinch valve 24, aspiration pinch valve 26, and calibration pinch valve 28. Irrigation circuit shown generally at 36 comprises first section 38 and second section 40. One end of second section 40 is adapted to contact eye 32. Aspiration circuit shown generally at 48 comprises lower section 49, third section 50, fourth section 52, and fifth section 54. Lower section 49 is adapted at one end to contact eye 32.

The workings of this ophthalmic irrigation/aspiration system 10 are clearly set forth in a co-pending patent application Ser. No. 09/173,451, filed Oct. 15, 1998, and titled Ophthalmic Aspiration System with Selectable Vent Method filed by inventors James Perkins, William Neubert, and Jeffery Knight and is hereby incorporated by reference in its entirety. Still further information is provided in a co-pending patent application Ser. No. 09/173,452, filed Oct.15, 1998, and titled Fluid Venting in Ophthalmic Irrigation/Aspiration System filed by inventors James Perkins and Jeffery Knight and hereby is incorporated in its entirety.

During fluid venting, pump 14 is stopped. Accordingly, no fluid enters in the pump inlet 55 through third section 50 nor exits pump outlet 56 to discharge directly into first opening 15 of bag 16. Aspiration pinch valve 26 closes and calibration pinch valve 28 is opened. Thus third section 50, fourth section 52, and fifth section 54 of aspiration circuit 48 are isolated from lower section 49 of aspiration circuit 48. The residual vacuum pressure existing in third section 50, fourth section 52, and fifth section 54 pulls air from second opening 17 of bag 16.

Thus, a portion of irrigation/aspiration circuit 18 is air vented.

In another example, pump 14 is stopped, aspiration pinch valve 26 closes, calibration pinch valve 28 opens, bridge pinch valve 24 is closed, and irrigation pinch valve 22 is open. As a result, air is drawn from second opening 17 of bag 16 to vent aspiration circuit 48. This results in a slight pressure differential between one end of second section 40 of irrigation circuit 36 and lower section 49 of aspiration circuit 48. A practical result of this slight pressure differential is that material is guided from the irrigation side to stay at the aspiration side of an irrigation/aspiration handpiece (not shown). This characteristic emulates air venting in irrigation/aspiration systems which do not utilize a positive displacement pump as is utilized and shown at 14 of ophthalmic irrigation/aspiration system 10.

Figure 2:
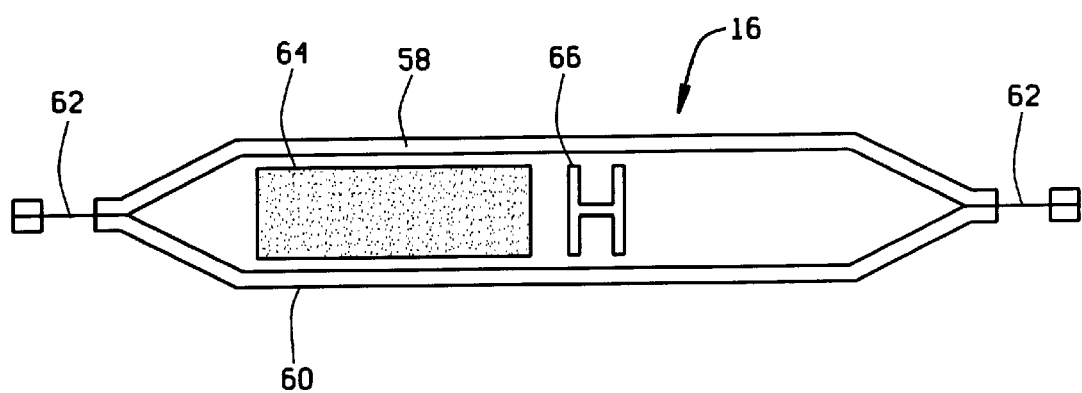
FIG. 2 illustrates a cross-section view of a bag in accordance with the present invention.

As shown in FIG. 2, bag 16 is formed from first wall 58 and second wall 60 joined together at weld 62. Disposed within bag 16 is a first air reservoir member 64 made from a cellular material, a sponge. Also, a second air reservoir member 66 may be disposed within bag 16 which is a spacing element that ensures a predetermined distanced separation between first wall 58 and second wall 60. While two reservoir members are shown in FIG. 2, it is preferred that only one air reservoir member be present within bag 16. In the preferred embodiment, first and second air reservoir members 64 and 66 provide sterile air in a volume sufficient to provide relief to the vacuum pressure demands in aspiration circuit 48.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A bag for use in an ophthalmic microsurgical system wherein the system has an aspiration circuit and a pump having an inlet and an outlet, in fluid communication with the aspiration circuit, the bag comprising:

a first wall;

a second wall joined to said first wall to form said bag;

an air reservoir member disposed within said bag to allow venting of the aspiration circuit; and a first opening for connection to the pump outlet and the aspiration circuit and a second opening for connection to the aspiration circuit and the pump inlet.

2. A bag according to claim 1, wherein said air reservoir contains sterile air.

3. A bag according to claim 1, wherein said air reservoir member is made from a cellular material.

4. A bag according to claim 3, wherein said cellular material is a sponge.

5. A bag according to claim 1, wherein said air reservoir member is a spacing element that ensures a predetermined distance separation between said first wall and said second wall.

* * * * *